Feb. 22, 1944. L. SPERA Plant Pat. 618
ROSE PLANT
Filed Aug. 12, 1943
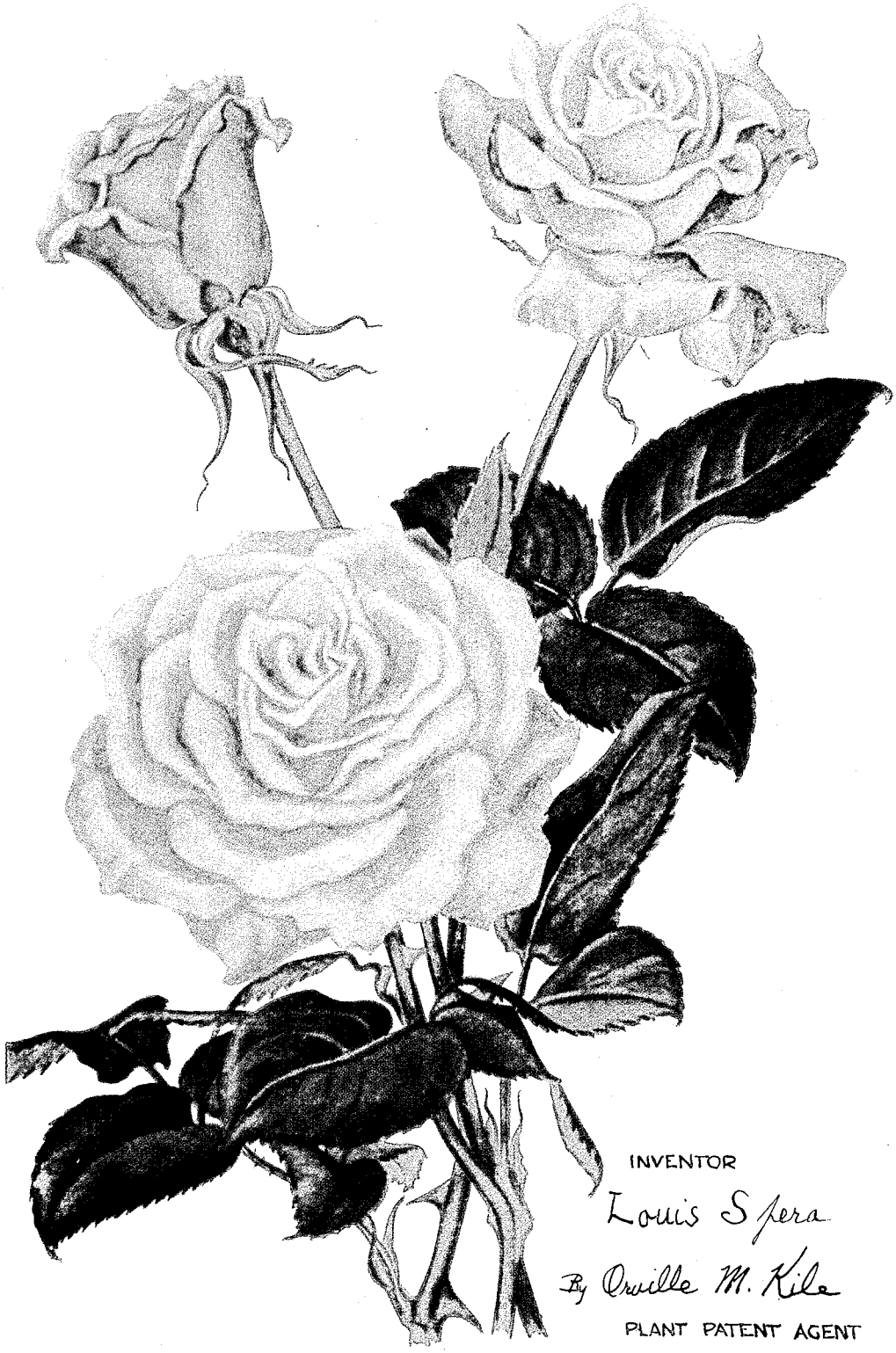
INVENTOR
Louis Spera
By Orville M. Kile
PLANT PATENT AGENT Patented Feb. 22, 1944

Plant Pat. 618

UNITED STATES PATENT OFFICE

618

ROSE PLANT

Louis Spera, Madison, N. J., assignor to Rose Farms Corporation, Chatham Township, Morris County, N. J., a corporation of New Jersey Application August 12, 1943, Serial No. 498,343

1 Claim. (Cl. 47—61)

My new discovery relates to improvements in hybrid tea rose varieties and pertains particularly to differences in color, size, shape and texture of blossom and color, size and substance of foliage as compared with its parent, now known as Pink Delight but formerly called Vierlanden. The color of the blossom is much darker, being definitely in the red class and somewhat similar to Better Times in the bud stage. The blossom is more globular and larger than that of its parent, and the petals are of heavier texture and they reflex more upon opening. The foliage is larger, darker and heavier than that of its parent, and the color of the wood is also darker.

While my new rose is also of the general type of Better Times, it is of different parentage and has a number of different characteristics, some of which I believe to be decided improvements. The color of the two roses is similar in the bud stage, but whereas the flower of Better Times becomes lighter and duller as it develops, the flower of my new variety becomes brighter and more lively in color and brilliance. The fragrance of my new rose is more pronounced and the texture of its petals is decidedly heavier than that of petals of Better Times, the latter quality no doubt contributing greatly to the exceptional keeping ability of my rose. Habits of growth of the two varieties differ somewhat as also do foliage and stem characteristics, one of the latter being that my variety produces much longer and heavier stems without pinching.

This new variety was discovered by me in the greenhouses of the Rose Farms Corporation at Madison, N. J., as a sport growing on a plant of Pink Delight (formerly Vierlanden). I have asexually reproduced it for some time and its characteristics have proved to be permanently fixed.

The original illustration which is a part of this specification shows three greenhouse-grown blossoms of this new variety, the paintings having been made from roses shipped to Washington. A portion of the stems and leaves is also shown. These paintings are in approximately the true colors although the velvety brilliance of the flowers could not be adequately shown by means of water colors.

In the following detailed description, color plate references indicate Ridgway's Color Standards and Nomenclature. This description is based upon specimens grown in our greenhouses at Madison and cut in the month of May.

*The plant*

Growth habits: Very vigorous upright bush with exceedingly long and strong stems. So far as I have been able to observe, its growth characteristics are similar to those of its parent.

Blooming habit: Continuous and prolific.

Foliage: Abundant. Leaves compound, with 3 to 5 leaflets.

*Size.*—Large. Terminal leaflet 3¼ inches long by 2 inches wide.

*Shape.*—Ovate, with sharply serrated edge and acuminate apex.

*Texture.*—Heavy and leathery.

*Color.*—Very dark green—between Dark Dull Yellow Green (Plate XXXII) and Empire Green (Plate XXXII). Under surface is Light Elm Green (Plate XVII).

Rachis: Relatively short; deeply grooved and red-tinged above; some spines on under side.

Stipules: Narrow; moderate in length; clinging except for long sharp ends; usually simple but occasionally foliaceous.

Stems: Very long, heavy and strong; numerous large thorns; Dark Cress Green (Plate XXXI), usually with reddish tinge on a portion of stem.

*Internodes.*—Short, bringing foliage close together.

*Thorns.*—Many; large; downward-pointing; irregularly spaced; very sharp-pointed; greenish white with brown tinge.

*The flower*

Bud:

*Shape.*—Long; urn-shaped.

*Size.*—Large; 1½ to 1¾ inches long.

*Color.*—Between Rose Red and Tyrian Rose (Plate XII); highly brilliant.

*Aspect.*—Silky outer surface.

*Sepals.*—Simple, sometimes slightly foliaceous; reflex early.

*Peduncle.*—Short; smooth; slightly lighter in color than the stems.

*Opening.*—Slow and very even.

Blossom:

*Form.*—Imbricated; high-centered, almost globular. As flower opens petals reflex slightly and become wavy. Stamens and pistils are seldom visible.

*Size.*—Large; at least 4 inches in diameter as an average.

*Petalage.*—Double, average about 28 petals.

*Color.*—The color is pretty uniformly spread over the blossom, particularly in its early stages, although there is a little variation between specimens. Looking into a partly opened bud it appears very dark and velvety, between Tyrian Rose and Amaranth Purple (Pl. XII). The color of the fully opened rose is a deep bright cerise. This lies between Rose Color and Tyrian Rose (Pl. XII), coming very close to the latter but with a velvety brilliance shown neither in the Color Guide nor adequately in the illustration. After several days, the color approaches Rose Color (Pl. XII).

Petals:

*Size.*—Large. Outer petals 2½ inches broad and 2 inches from point of attachment to tip. Intermediate petals are much smaller.

*Shape.*—Outer petals broadly obovate, intermediate petals almost round.

*Texture.*—Exceptionally substantial.

*Appearance.*—Silky on outer surface; velvety on inner surface.

*Fragrance.*—Delightfully fragrant. Has more fragrance than most roses known to me.

*Lasting qualities.*—Excellent. Lasts many days after being cut.

*Behavior.*—Petals cling until dead.

Reproductive organs:

*Pistils.*—Many; tightly bunched. *Styles*—short; color between Tyrian Rose and Pomegranate Purple (Plate XII). *Stigmas*—small; cream-colored.

*Stamens.*—Many; loosely bunched about pistils. *Filaments*—uneven in length but all much longer than styles; Deep Rose Pink (Plate XII. *Anthers*—medium in size; center same color as filaments, edges Light Tan. *Pollen*—Bright Yellow.

Having thus disclosed my discovery, I claim: The new and distinct variety of hybrid tea rose plant substantially as herein shown and described, characterized particularly by its combination of bright Rose Red to Tyrian Rose blossoms of exceptionally heavy texture, large size, excellent form, delightful abundant fragrance, and excellent keeping qualities; its large heavy dark green foliage; and its long, robust and rigid stems.

LOUIS SPERA.